United States Patent [19]

Stammer

[11] Patent Number: 4,629,784

[45] Date of Patent: Dec. 16, 1986

[54] SYNTHESIS OF CYCLOPROPANE AMINO ACIDS

[75] Inventor: Charles H. Stammer, Athens, Ga.

[73] Assignee: The University of Georgia Research Foundation, Inc., Athens, Ga.

[21] Appl. No.: 677,901

[22] Filed: Dec. 5, 1984

Related U.S. Application Data

[63] Continuation of Ser. No. 523,808, Aug. 16, 1983, abandoned.

[51] Int. Cl.$^4$ ............... C07K 5/08; C07K 5/10; C07K 7/06
[52] U.S. Cl. ............... 530/328; 530/329; 530/330; 530/331
[58] Field of Search ............... 260/112.5 R; 530/328, 530/329, 330, 331

[56] References Cited

U.S. PATENT DOCUMENTS

| | | | |
|---|---|---|---|
| 3,050,559 | 8/1962 | Burger | 564/307 |
| 4,254,106 | 3/1981 | Wilkinson | 530/302 |
| 4,273,704 | 6/1981 | Mazur | 530/302 |
| 4,367,344 | 1/1983 | Gallenkamp | 560/115 |

OTHER PUBLICATIONS

Journal of Organic Chemistry, vol. 48, 1983, pp. 2440-2441, Kimura, et al.
Journal Heterocyclic Chemistry, vol. 20, 1983, pp. 607-613, Arenal, et al.
Monatshefte fur Chemie, vol. 103, 1972, pp. 288-291, Bregovee, et al.
Journal of Organic Chemistry, vol. 48, 1983, pp. 4769-4771, Suzuki et al.
Journal of Organic Chemistry, vol. 47, 1982, pp. 3270-3273, King et al.
Biochemical and Biophysical Research Communications, vol. 115, No. 1, 1983, pp. 112-115, Kimur et al.
Chemical Abstract, vol. 98, 1983, p. 197626m, Prochazka et al.
Aust. J. Chem. 1983, vol. 36, pp. 1629-1638, Stewart.
Aust. J. Chem. 1981, vol. 34, pp. 2431-2438, Stewart.
Journal F. Prakt. Chemie, Band 316, Heft 3, 1974, S. 363-8, Elkashef et al.
Anales De Quimica, vol. 77, 1980, pp. 93-95.
Agric. Biol. Chem., vol. 41, No. 12, 1977, pp. 2497-2498, Shiraishi et al.
Eur. J. Med. Chem.-Chimica Therapeutica, 1979, vol. 14, pp. 33-45, Bernabf et al.
Eur. J. Med. Chem.-Chimica Therapeutica, 1980, vol. 15, No. 2, pp. 139-146, Grouiller et al.
Tetrahedron Letters, vol. 24, No. 36, pp. 3839-3840, 1983, Suzuki et al.
Tetrahedron Letters, vol. 24, No. 21, pp. 2193-2194, 1983, Horikawa et al.
Journal of Organic Chemistry, 1984, vol. 49, pp. 1634-1636, Bland et al.
J. Am. Chem. Soc., vol. 102, No. 7, 1980, pp. 2463-2464, Jung et al.
J. Am. Chem. Soc. vol. 99, No. 2, 1977, pp. 636-637, Ichihara et al.
Synthesis, vol. 3, 1977, pp. 191-193, Bernabe et al.
Stephen Wayne King, University of Georgia Ph.D. thesis, Part I: Analogues of Aspartame Part II: Cyclopropyl Amino Acids. Part III: The Use of DMAP Towards the Synthesis of Dehydro and Cyclopropyl Peptides, 1981.

*Primary Examiner*—Delbert R. Phillips
*Attorney, Agent, or Firm*—Gregor N. Neff

[57] ABSTRACT

Cyclopropane ("Cyclopropyl") amino acids and peptides containing at least one cyclopropyl amino acid are disclosed. The processes for synthesizing cyclopropyl amino acids and peptides containing at least one cyclopropyl amino acid are also disclosed. Cyclopropyl amino acids are useful as enzyme inhibitors and as substitutes for natural amino acids in peptide hormones such as regulators of bodily functions to enhance bioactivity, to stabilize the peptide into which it is incorporated to cleavage by enzymes and to convert such peptides into enzyme inhibitors.

29 Claims, No Drawings

SYNTHESIS OF CYCLOPROPANE AMINO ACIDS

The Government has rights in this invention pursuant to NIH Grant No. DA 02938 awarded by the Department of Health and Human Services.

This application is a continuation of application Ser. No. 523,808, filed Aug. 16, 1983, now abandoned.

BACKGROUND AND SUMMARY OF THE INVENTION

This invention relates to a process for preparing "cyclopropyl" amino acids ($\nabla$AA), defined as $\nabla$-amino acids in which the $C_\alpha$—$C_\beta$ bond is one side of a cyclopropane ring. These amino acids are useful as enzyme inhibitors and as substitutes for natural amino acids in peptide hormones (regulators of bodily functions) to enhance bioactivity, to stablilize the peptide to cleavage by enzymes and to convert these peptides into enzyme inhibitors.

The only process described in the literature (1)+(2)→(3)→(4) and related to the disclosed process is the addition of $CH_2N_2$ (1, $R^1 = R^2 = H$) to (2). (I. Bregovec and T. Jakovcic, Monats fur Chemie, 1972 103, 288). The commonly known addition of $CH_2N_2$ to unsaturated azlactones (M. Bernabe, et al., Ann de Quimica 1972, 68, 501, 1055; Eur. J. Med. Chem. 1979, 14, 44; Syn. Comm. 1977 191; J. Heterocyclic Chem. 1983, 20, 607; Pages, R. A., Burger, A.; J. Med. Chem., 1966, 9, 766; Awad, W. I. et al. Tetrahedron, 1964, 20, 891) is similar but not the same as the process of the present invention which requires the addition of a substituted diazomethane specifically to a dehydroalanine deriva-tive which must be synthesized for this purpose. The initial product is a 5-substituted pyrazoline which is then converted into the $\nabla$AA. In the process described in the literature, the initial product is a 4-substituted pyrazoline. The process of the present invention generates chiral cyclopropyl amino acids directly. This means that, if chirality is present in the dehydroalanine derivative, optically active cyclopropyl amino acids can be prepared directly without the necessity of resolution. This is not possible in the other processes reported.

New stereo specific cyclopropyl amino acids are disclosed. Also new peptides containing at least one stereo specific cyclopropyl amino acid are disclosed. The present invention describes a new process for synthesizing stereo specific cyclopropyl amino acids. Additionally, this new process can be used as part of a process for synthesizing peptides containing at least one stereo specific cyclopropyl amino acid residue. The term "amino acid" is understood to include analogs, derivatives, and congeners of any specific amino acid referred to herein.

It is an object of the present invention to provide new stereo specific cyclopropyl amino acids.

It is a further object to provide new peptides containing at least one stereo specific cyclopropyl amino acid residue.

These and other objects, aspects, and advantages of this invention will become apparent from a consideration of the accompanying specification and claims.

DESCRIPTION OF THE PREFERRED EMBODIMENTS

The process of the present invention is carried out by allowing a diazo compound (1), in the presence or absence of a catalyst or light, to react with a dehydroalanine derivative (2). The initial reaction product may be a pyrazoline derivative (3) which is pyrolyzed, photolyzed or treated with a catalyst to give the cyclopropyl amino acid derivative (4). The reaction is as shown in equations A and B, below:

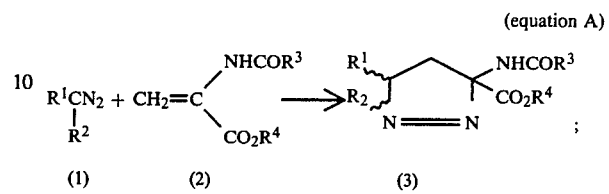

(equation A)

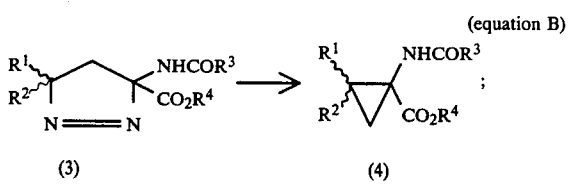

(equation B)

The product (4), a cyclopropyl amino acid derivative, may consist of a mixture of stereoisomers which are separable by physical means into the E- and Z-diastereomers. Each of these diastereomers consists of a pair (2R, 2S) of enantiomers which can be separated by standard resolution methods. Separation into E- and Z-diastereomers and separation of the enantiomers may occur either before or after deblocking the product (4).

Compound (1): $R^1$ and $R^2$ can be hydrogen, an alkyl (aliphatic) group, an aromatic group (aryl such as phenyl, indolyl, imidazolyl or the like), an alkyl group substituted by a halogen, oxygen, nitrogen, or sulfur, an alkyl group substituted by an aromatic group, or an aromatic group substituted by a halogen, oxygen, nitrogen, sulfur aromatic or aliphatic group except that $R^1$ and $R^2$ are not both hydrogen in the diazo compound.

Compound (2): $R^3$ can be any alkyl or aromatic group or alkoxy or aryloxy group. $R^4$ can be any alkyl or aryl group.

The solvent used in the reaction can be any aprotic solvent, such as $CHCl_3$, $CH_2Cl_2$, tetrahydrofuran, dioxane, diethyl ether, etc. or protic solvent such as methanol or ethanol.

The reaction temperature (first step) is 0°–30° C. and that of the second step may be 0°–150° C. A solvent such as benzene or toluene or the like may be used in the second step.

For purposes of obtaining the free cyclopropyl amino acid (AA), compound (4) may be C-terminal deblocked, depending on the nature of $R_3$, by standard procedures such as saponification or hydrogenolysis giving the acid (5) as shown in equation C, below:

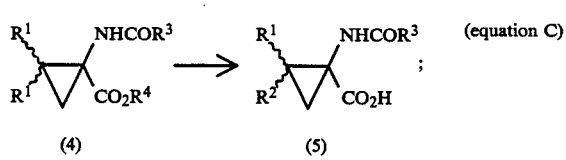

(equation C)

and N-terminal deblocking of (5) by the use of anhydrous acid, dry HCl or $CF_3CO_2H$, by hydrogenolysis or by hydrolysis, depending on the nature of $R^3$, can be accomplished by standard procedures as shown in equation D, below:

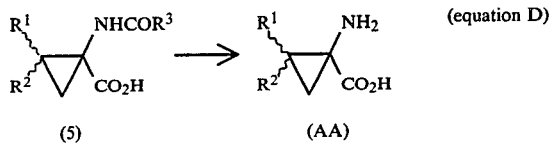 (equation D)

Deblocking of the amino group (N-terminal deblocking) as shown in equation E, below, may precede deblocking of the carboxyl group (C-terminal deblocking) (equation C) resulting in a cyclopropyl amino acid.

This invention discloses a process for synthesizing a cyclopropyl amino acid selected from the group consisting of (2S)-E-, (2R)-E-, (2S)-Z-, (2R)-Z-, (2S)-, (2R)-, (2RS)-E-, and (2RS)-Z-isomers wherein the cyclopropyl amino acid is selected from the group consisting of cyclopropyl amino acids, analogs, derivatives, and congeners thereof comprising the following steps:

(a) reacting a diazo compound having the formula wherein $R^1R^2CN_2$ wherein $R^1$ is selected from the group consisting of hydrogen, an alkyl group, an aromatic group, an alkyl group substituted by a halogen, oxygen, nitrogen, or sulfur, an alkyl group substituted by an aromatic group, and an aromatic group substituted by a halogen, oxygen, nitrogen, sulfur aromatic or aliphatic group, wherein $R^2$ is selected from the group consisting of hydrogen, an alkyl group, an aromatic group, an alkyl group substituted by a halogen, oxygen, nitrogen, or sulfur, an alkyl group substituted by an aromatic group and an aromatic group substituted by a halogen, oxygen, nitrogen, sulfur aromatic or aliphatic group, and wherein $R^1$ and $R^2$ are not both hydrogen in the diazo compound with a dehydroalanine derivative having the formula

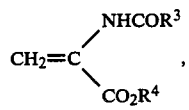

wherein $R^3$ is selected from the group consisting of an alkyl group, an aromatic group, an alkoxy group, and an aryloxy group and wherein $R^4$ is selected from the group consisting of an alkyl group and an aryl group to produce an initial reaction product;

(b) decomposing the initial reaction product to produce a cyclopropyl amino acid derivative having the formula

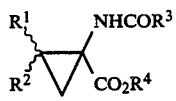

wherein the cyclopropyl amino acid derivative is a mixture of stereoisomers;

(c) separating the mixture of stereoisomers by physical means into E- and Z-diastereomers wherein the E- and Z-diastereomers comprise a pair of enantiomers;

(d) separating the pair of enantiomers by standard resolution means to produce a stereo specific cyclopropyl amino acid derivative;

(e) deblocking the initial reaction product to produce a stereo specific cyclopropyl amino acid having the formula

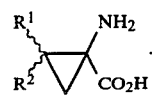

If $R^1$ or $R^2$ contain acidic groups selected from the group consisting of carboxyl, mercapto, and phenolic hydroxyl, $R^1$ and $R^2$ are blocked by standard means to protect such groups during the process. Synthesis of the following cyclopropyl amino acids requires such blocking; aspartic acid, tyrosine, 3-4-dihydroxyphenylalanine (DOPA), 5-hydroxytryptophan, cysteine, and homocysteine. If $R^3$ or $R^4$ of the dehydroalanine derivative is optically active, an optically active stereo specific cyclopropyl amino acid can be produced without step (d) of the process. The diazo compound is reacted with the dehydroalanine derivative in the presence or absence of a catalyst and in the presence or absence of light. Pyrolysis, photolysis, or catalytic decomposition can be used to decompose the initial reaction product. A solvent selected from the group consisting of an aprotic solvent and a protic solvent can be used in the process. The step producing the initial reaction product is carried out at a temperature range of 0° C. through 30° C., and the step producing the cyclopropyl amino acid derivative is carried out at a temperature range of 0° C. through 150° C. When pyrolysis is used to decompose the initial reaction product, a solvent selected from the group consisting of benzene, toluene, and a similar solvent can be used in the step producing the cyclopropyl amino acid derivative. If the stereo specific cyclopropyl amino acid derivative is C-terminal deblocked to produce a stereo specific cyclopropyl acid having the formula

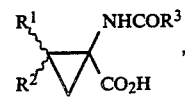

saponification or hydrogenolysis can be used to C-terminal deblock the stereo specific cyclopropyl acid derivative. After C-terminal deblocking, the stereo specific cyclopropyl acid is N-terminal deblocked to produce the stereo specific cyclopropyl amino acid. Anhydrous acid, the stereo specific cyclopropyl acid, dry hydrogen chloride, trifluoroacetic acid, hydrogenolysis, the stereo specific cyclopropyl acid, or hydrolysis can be used to N-terminal deblock the stereo specific cyclopropyl acid. N-terminal deblocking can precede carboxyl terminal deblocking to produce the stereo specific amino acid. Steps (c) and (d) of the process described above can be carried out before or after deblocking.

For purposes of preparing peptides, compound (5), $R^3=OCH_2Ph$ or $OC(CH_3)_3$, is prepared. Standard coupling methods, mixed anhydride, carbodiimide, etc., are used to couple (5) with C-terminal blocked amino acids or peptides. N-terminal deblocking of (4) to give (6) is accomplished using anhydrous acids, dry. HCl or $CF_3CO_2H$, or hydrogenolysis depending on the natures of $R^3$ and $R^4$ as shown in equation E, below:

$$\underset{(4)}{\overset{R^1}{\underset{R^2}{\bigtriangledown}}\overset{NHCOR^3}{\underset{CO_2R^4}{}}} \longrightarrow \underset{(6)}{\overset{R^1}{\underset{R^2}{\bigtriangledown}}\overset{NH_2}{\underset{CO_2R^4}{}}} \quad \text{(equation E)}$$

Compound (6) is useful in coupling with N-blocked carboxyl-activated amino acids or peptides to form desired peptides.

This invention discloses a process for synthesizing peptides having at least two and not more than twenty amino acid residues selected from the group consisting of D- or L-isomers of amino acid residues wherein amino acid residues are selected from the group consisting of amino acid residues, analogs, derivatives, and congeners thereof and wherein at least one amino acid residue is a stereo specific cyclopropyl amino acid residue selected from the group consisting of cyclopropyl amino acid residues, analogs, derivatives, and congeners thereof comprising the following steps:

(a) synthesizing the cyclopropyl amino acid derivative utilizing steps (a) and (b) of the process described above for synthesizing stereo specific cyclopropyl amino acids;

(b) separating the stereo specific cyclopropyl amino acid utilizing steps (c) and (d) of the process described above for synthesizing stereo specific cyclopropyl amino acids;

(c) deblocking the stereo specific cyclopropyl amino acid derivative by standard means to produce an N-terminal blocked stereo specific cyclopropyl amino acid;

(d) coupling the N-terminal blocked stereospecific cyclopropyl amino acid with a C-terminal blocked amino acid or peptide; and (e) repeating the above steps as necessary to produce a desired peptide.

Step (c), the deblocking, can be carried out before step (b), the separation step.

An alternate process for synthesizing peptides utilizes stereo specific cyclopropyl acids generated as described above comprises the following steps:

(a) N-terminal blocking the stereo specific cyclopropyl amino acid by standard means to produce the N-terminal blocked stereo specific cyclopropyl amino acid;

(b) coupling the N-terminal blocked stereo specific cyclopropyl amino acid with a C-terminal blocked amino acid or peptide; and (c) repeating the above steps as necessary to produce a desired peptide having at least two and not more than twenty amino acid residues selected from the group consisting of D- or L-isomers of amino acid residues wherein amino acid residues are selected from the group consisting of amino acid residues, analogs, derivatives, and congeners thereof and wherein at least one amino acid residue is a stereo specific cyclopropyl amino acid residue selected from the group consisting of cyclopropyl amino acid residues, analogs, derivatives, and congeners thereof.

A second alternate process for synthesizing peptides having at least two and not more than twenty amino acid residues selected from the group consisting of D- or L-isomers of amino acid residues wherein amino acid residues are selected from the group consisting of amino acid residues, analogs, derivatives, and congeners thereof and wherein at least one amino acid residue is a stereo specific cyclopropyl amino acid residue selected from the group consisting of cyclopropyl amino acid residues, analogs, derivatives, and congeners thereof comprises the following steps:

(a) synthesizing a cyclopropyl amino acid utilizing steps (a), (b), and (e) of the process described above for synthesizing stereo specific cyclopropyl amino acids;

(b) N-terminal blocking the cyclopropyl amino acid by standard means to produce a N-terminal blocked cyclopropyl amino acid;

(c) separating the stereo specific cyclopropyl amino acid utilizing steps (c) and (d) of the process described above for synthesizing stereo specific cyclopropyl amino acids;

(d) coupling the N-terminal blocked stereospecific cyclopropyl amino acid with a C-terminal blocked amino acid or peptide; and (e) repeating the above steps as necessary to produce a desired peptide.

Step (c) of this second alternate process for synthesizing peptides can be carried out before step (b) of same.

A third alternate process for synthesizing peptides having at least two and not more than twenty amino acid residues selected from the group consisting of D- or L-isomers of amino acid residues wherein amino acid residues are selected from the group consisting of amino acid residues, analogs, derivatives, and congeners thereof and wherein at least one amino acid residue is a stereo specific cyclopropyl amino acid residue selected from the group consisting of cyclopropyl amino acid residues, analogs, derivatives, and congeners thereof comprises the following steps:

(a) synthesizing the cyclopropyl amino acid derivative utilizing steps (a) and (b) of the process described above for synthesizing stereo specific cyclopropyl amino acids;

(b) separating the stereo specific cyclopropyl amino acid utilizing steps (c) and (d) of the process described above for synthesizing stereo specific cyclopropyl amino acids;

(c) N-terminal deblocking the stereo specific cyclopropyl amino acid derivative by standard means to produce a C-terminal blocked amino acid;

(d) coupling the C-terminal blocked stereo specific cyclopropyl amino acid with a N-terminal blocked amino acid or peptide; and (e) repeating the above steps as necessary to produce a desired peptide.

Step (c) of this third alternate process for synthesizing peptides can be carried out before step (b) of same.

A fourth alternate process for synthesizing peptides utilizing stereo specific cyclopropyl amino acids generated as described above and comprising the following steps:

(a) C-terminal blocking the stereo specific cyclopropyl amino acid by standard means to produce the C-terminal blocked stereo specific cyclopropyl amino acid;

(b) coupling the C-terminal blocked stereo specific cyclopropyl amino acid with a N-terminal blocked amino acid or peptide; and (c) repeating the above steps as necessary to produce a desired peptide having at least two and not more than twenty amino acid residues selected from the group consisting of D- or L-isomers of amino acid residues wherein amino acid residues are selected from the group consisting of amino acid residues, analogs, derivatives, and congeners thereof and wherein at least one amino acid residue is a stereo specific cyclopropyl amino acid residue selected from the group consisting of cyclopropyl amino acid residues, analogs, derivatives, and congeners thereof.

A fifth alternate process for synthesizing a peptide having at least two and not more than twenty amino acid residues selected from the group consisting of D- or L-isomers of amino acid residues wherein amino acid residues are selected from the group consisting of amino acid residues, analogs, derivatives, and congeners thereof and wherein at least one amino acid residue is a stereo specific cyclopropyl amino acid residue selected from the group consisting of cyclopropyl amino acid residues, analogs, derivatives, and congeners thereof comprises the following steps:

(a) synthesizing a cyclopropyl amino acid utilizing steps (a), (b), and (e) of the process described above for synthesizing stereo specific cyclopropyl amino acids;

(b) C-terminal blocking the cyclopropyl amino acid by standard means to produce a C-terminal blocked cyclopropyl amino acid;

(c) separating the C-terminal blocked stereo specific cyclopropyl amino acid utilizing steps (c) and (d) of the process described above for synthesizing stereo specific cyclopropyl amino acids;

(d) coupling the C-terminal blocked stereo specific cyclopropyl amino acid with a N-terminal blocked amino acid or peptide; and (e) repeating the above steps as necessary to produce a desired peptide.

Step (c) of this fifth alternate process for synthesizing peptides can be carried out before step (b) of same.

A sixth alternate process for synthesizing peptides utilizes stereo specific amino acids generated as described above, wherein $R^3$ or $R^4$ of the dehydroalanine derivative is optically active and step (d) of such process described above for synthesizing stereo specific cyclopropyl amino acids is not required, comprises the following steps:

(a) N-terminal blocking the stereo specific cyclopropyl amino acid by standard means to produce the N-terminal blocked stereo specific cyclopropyl amino acid;

(b) coupling the N-terminal blocked stereo specific cyclopropyl amino acid with a C-terminal blocked amino acid or peptide; and (c) repeating the above steps as necessary to produce a desired peptide having at least two and not more than twenty amino acid residues selected from the group consisting of D- or L-isomers of amino acid residues wherein amino acid residues are selected from the group consisting of amino acid residues, analogs, derivatives, and congeners thereof and wherein at least one amino acid residue is a stereo specific cyclopropyl amino acid residue selected from the group consisting of cyclopropyl amino acid residues, analogs, derivatives, and congeners thereof.

A seventh alternate process for synthesizing peptides utilizes stereo specific amino acids generated as described above, wherein $R^3$ or $R^4$ of the dehydroalanine derivative is optically active and step (d) of such process described above for synthesizing stereo specific cyclopropyl amino acids is not required, comprises the following steps:

(a) C-terminal blocking the stereo specific cyclopropyl amino acid by standard means to produce the C-terminal blocked stereo specific cyclopropyl amino acid;

(b) coupling the C-terminal blocked stereo specific cyclopropyl amino acid with a N-terminal blocked amino acid or peptide; and (c) repeating the above steps as necessary to produce a desired peptide having at least two and not more than twenty amino acid residues selected from the group consisting of D- or L-isomers of amino acid residues wherein amino acid residues are selected from the group consisting of amino acid residues, analogs, derivatives, and congeners thereof and wherein at least one amino acid residue is a stereo specific cyclopropyl amino acid residue selected from the group consisting of cyclopropyl amino acid residues, analogs, derivatives, and congeners thereof.

This invention discloses novel stereo specific cyclopropyl amino acids selected from the group consisting of (2S)-E-, (2R)-E-, (2S)-Z-, (2R)-Z-, (2S)-, (2R)-, (2RS)-E-, and (2RS)-Z-isomers wherein the cyclopropyl amino acids are selected from the group consisting of cyclopropyl amino acids, analogs, derivatives, and congeners thereof having the formula

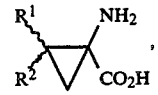

wherein $R^1$ is selected from the group consisting of hydrogen, an alkyl group, an aromatic group, an alkyl group substituted by a halogen, oxygen, nitrogen, or sulfur, an alkyl group substituted by an aromatic group, and an aromatic group substituted by a halogen, oxygen, nitrogen, sulfur aromatic or aliphatic group, wherein $R^2$ is selected from the group consisting of hydrogen, an alkyl group, an aromatic group, an alkyl group substituted by a halogen, oxygen, nitrogen, or sulfur, an alkyl group substituted by an aromatic group and an aromatic group substituted by a halogen, oxygen, nitrogen, sulfur aromatic or aliphatic group, wherein $R^1$ and $R^2$ are not both hydrogen, wherein $R^1$ and $R^2$ are not $C_6H_5$ and H, respectively, or H and $C_6H_5$, respectively, wherein $R^1$ and $R^2$ are not 4-$HOC_6H_4$ and H, respectively, or H and 4-$HOC_6H_4$, respectively, and wherein $R^1$ and $R^2$ are not 4(5)-imidazolyl and H, respectively, or H and 4(5)-imidazolyl, respectively.

Cyclopropyl amino acids (AA) which can be made according to this invention are shown in Table I, below.

TABLE I

Amino Acids:

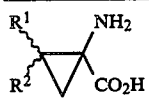

| $R^1$ | $R^2$ | ∇AA (novel compounds indicated by "*") |
|---|---|---|
| $CH_3$ | $CH_3$ | *Valine |
| $(CH_3)_2CH$ | H | *Leucine |

TABLE I-continued

Amino Acids:

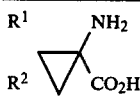

| R¹ | R² | ∇AA (novel compounds indicated by "*") |
|---|---|---|
| H | (CH₃)₂CH | *Leucine |
| CO₂H | H | *Aspartic acid |
| H | CO₂H | *Aspartic acid |
| CH₂CO₂H | H | *Glutamic acid |
| H | CH₂CO₂H | *Glutamic acid |
| CH₂CO | H | *pyroGlutamic acid |
| CH₃SCH₂ | H | *Methionine |
| H | CH₃SCH₂ | *Methionine |
| NH₂(CH₂)₃ | H | *Lysine |
| H | NH₂(CH₂)₃ | *Lysine |
| NH₂C(=NH)—NHCH₂CH₂ | H | *Arginine |
| H | NH₂C(=NH)—NHCH₂CH₂ | *Arginine |
| NH₂(CH₂)₂ | H | *Ornithine |
| H | NH₂(CH₂)₂ | *Ornithine |
| C₆H₅ | H | Phenylalanine |
| H | C₆H₅ | Phenylalanine |
| 4-HOC₆H₄ | H | Tyrosine |
| H | 4-HOC₆H₄ | Tyrosine |
| 3,4(HO)₂C₆H₃ | H | *3,4 Dihydroxyphenylalanine |
| H | 3,4(HO)C₆H₃ | *3,4 Dihydroxyphenylalanine |
| 3-indolyl | H | *Tryptophan |
| H | 3-indolyl | *Tryptophan |
| 5-hydroxy-3-indoyl | H | *Hydroxytryptophan |
| H | 5-hydroxy-3-indoyl | *Hydroxytryptophan |
| HO | H | *Serine |
| H | HO | *Serine |
| HS | H | *Cysteine |
| H | HS | *Cysteine |
| HSCH₂ | H | *Homocysteine |
| H | HSCH₂ | *Homocysteine |
| HOCH₂ | H | *Homoserine |
| H | HOCH₂ | *Homoserine |
| 4(5)-imidazolyl | H | *Histidine |
| H | 4(5)-imidazolyl | *Histidine |
| (CH₂)ₙ wherein n = 1, 3, or 4 | H | *Proline |
| (CH₂)₂ wherein n = 2 | H | *Proline |

Except for valine, pyroGlutamic acid, proline, and proline analogs, the above cyclopropyl amino acids are shown as E- and Z-diastereomers. It is understood that all of the above listed cyclopropyl amino acids have (2R)- and (2S)-enantiomers.

Peptides having at least two but not more than twenty amino acid residues selected from the group consisting of D- or L-isomers of amino acid residues wherein the amino acid residues are selected from the group consisting of amin acid residues, analogs, derivatives, and congeners thereof, can be prepared according to the methods disclosed wherein the amino acid residues are selected from the group consisting of amino acid residues, analogs, derivatives, and congeners thereof, wherein at least one amino acid residue is a stereo specific cyclopropyl amino acid residue selected from the group consisting of (2S)-E-, (2R)-E, (2S)-Z-, (2R)-Z-, (2S)-, and (2R)-isomers, wherein the cyclopropyl amino acid residue is selected from the group consisting of cyclopropyl amino acid residues, analogs, derivatives, and congeners thereof, and wherein the stereo specific cyclopropyl amino acid residue is not alanine. Examples of such peptides are shown in Table II, below.

TABLE II

Peptides:
It is understood that all possible stereoisomers are included although not actually described.

| R¹—R² | R¹—R²—R³ |
|---|---|
| ∇Asp—Phe.OCH₃ | ∇Met—Leu—Phe |
| Asp—∇Phe.OCH₃ | Met—∇Leu—Phe |
| ∇Asp—∇Phe.OCH₃ | Met—Leu—∇Phe |
| | pGln—His—∇Pro—NH₂ |
| | pGln—∇His—Pro—NH₂ |
| | ∇pGln—His—Pro—NH₂ |

| R¹—R²—R³—R⁴—R⁵—R⁶—R⁷—R⁸ | |
|---|---|
| Asp—Arg—Val—Tyr—Ile—His—Pro—∇Phe | Phe.OCH₃—phenylalanine methyl ester |
| Asp—Arg—Val—Tyr—Ile—∇His—Pro—Phe | Arg—arginine |
| Asp—Arg—Val—∇Tyr—Ile—His—Pro—Phe | Asp—aspartic acid |

∇—cyclopropyl

TABLE II-continued

Peptides:
It is understood that all possible stereoisomers are included although not actually described.

| | |
|---|---|
| Asp—Arg—∇Val—Tyr—Ile—His—Pro—Phe | pGlu—pyroglutamic acid |
| Asp—∇Arg—Val—Tyr—Ile—His—Pro—Phe | Gly—glycine |
| ∇Asp—Arg—Val—Tyr—Ile—His—Pro—Phe | His—histidine |
| Asp—Arg—Val—∇Tyr—Ile—His—Pro—∇Phe | Ile—isoleucine |
| Asp—Arg—Val—∇Tyr—Ile—∇His—Pro—Phe | Leu—leucine |
| Asp—Arg—Val—Tyr—Ile—∇His—Pro—∇Phe | Met—methionine |
| Sar—Arg—Val—∇Tyr—Ile—His—Pro—Phe | Phe—phenylalanine |
| Sar—Arg—Val—Tyr—Ile—∇His—Pro—Phe | Pro—proline |
| Sar—Arg—Val—Tyr—Ile—His—Pro—∇Phe | Pro—NH₂—proline amide |
| Sar—Arg—Val—Tyr—Ile—∇His—Pro—∇Phe | Sar—sarcosine |
| Sar—Arg—Val—∇Tyr—Ile—∇His—Pro—Phe | Ser—serine |
| Sar—Arg—Val—∇Tyr—Ile—∇His—Pro—∇Phe | Tyr—tyrosine |
| Sar—Arg—Val—∇Tyr—Ile—His—Pro—∇Phe | Val—valine |

R¹—R²—R³—R⁴—R⁵—R⁶—R⁷

Pro—Phe—His—∇Leu—Leu—Val—Tyr
Pro—Phe—His—Leu—∇Leu—Val—Tyr
Pro—∇Phe—His—Leu—∇Leu—Val—Tyr
Pro—∇Phe—His—∇Leu—Leu—Val—Tyr

R¹—R²—R³—R⁴—R⁵—R⁶

Ile—His—Pro—∇Phe—His Leu
Ile—His—Pro—Phe—∇His—Leu

R¹—R²—R³—R⁴—R⁵—R⁶—R⁷—R⁸—R⁹

Arg—Pro—Pro—Gly—Phe—Ser—Pro—∇Phe—Arg
Arg—Pro—Pro—Gly—∇Phe—Ser—Pro—Phe—Arg
Arg—Pro—Pro—Gly—∇Phe—Ser—Pro—∇Phe—Arg

R¹—R²—R³—R⁴—R⁵

Tyr—Gly—Gly—∇Phe—Leu
Tyr—Gly—Gly—∇Phe—Met
Tyr—D—Ala—Gly—∇Phe—Met
Tyr—D—Ala—Gly—∇Phe—Leu
∇Tyr—Gly—Gly—Phe—Leu
∇Tyr—D—Ala—Gly—Phe—Leu
∇Tyr—D—Ala—Gly—Phe—Met
∇Tyr—Gly—Gly—∇Phe—Leu
∇Tyr—Gly—Gly—∇Phe—Met
Tyr—Gly—Gly—Phe—∇Leu
Tyr—D—Ala—Gly—Phe—∇Leu
∇Tyr—D—Ala—Gly—Phe—∇Leu
Tyr—Gly—Gly—Phe—∇Met
Tyr—D—Ala—Gly—Phe—∇Met
∇Tyr—D—Ala—Gly—Phe—∇Met
∇Tyr—Gly—Gly—Phe—∇Met
∇Tyr—Gly—Gly—Phe—∇Leu

EXAMPLE I

Boc-Ser.OBz1O(N₂) (1)

Boc-Ser.OH (0.097 mol) was dissolved in ethyl acetate (140 ml) and p-nitrobenzyl bromide (21 g, 0.097 mol) followed by triethylamine (9.7 g, 0.097 mol) were added to the mixture, which was refluxed for 18 hr. After cooling, water (200 ml) was added to the reaction mixture, the layers were separated and the aqueous layer was extracted with AcOEt. The extracts were washed with 5% NaHCO₃ soln. (100 ml), sat. NaCl soln, dried over Na₂SO₄ and evaporated in vacuo. The resulting pale yellow oil was dissolved in Et₂O (100 ml) and kept in refrigerator for 4 hr. The colorless crystals were filtered by suction to give Boc-Ser.OBz1(NO₂) (1) (18.0 g, 54.5%) as prisms; from the filtrate, a 2nd crop weighing 3.5 g was obtained (total yield 65%); mp 92°–93° C.; IR: (KBr) 3320–3420 (NH,OH), 1745 (C=O), 1660 (C=O). NMR (CDCl₃)δ: 8.2 and 7.2 (AB d, J=12 Hz, 4H, ArH). 5.5 (br, d, 1H, NH), 5.25 (s, 2H, OCH₂) 4.25–4.5 (m, 1H, CH), 3.90 (d, 2H, CH₂OH), 2.60 (br, 1H, OH), 1.38 (s, 9H, Boc).

EXAMPLE II

Boc-Dehydroalanine-p-nitrobenzyl ester (2)

(a) Using-EDC

To a suspension of Boc-Ser.OBz1(NO₂) (1) (6.0 g, 0.0176 mol) and CuCl (1.8 g, 0.018 mol) in CHCl₃ (180 ml) was added 1-ethyl-3(3-dimethylaminopropyl)-carbodiimide hydrochloride (EDC, 4.14 g, 0.0216 mol) at room temperature. The mixture was stirred overnight at room temperature during which time a brown oil separated. Water (150 ml) was added and the CHCl₃ layer was separated and washed with water, dried over Na₂SO₄, and evaporated in vacuo. The resulting solid was recrystallized from ethyl acetate-n-hexane to give colorless prisms 4.5 g (79.3%) of Boc-dehydroalanine-p-nitrobenzyl ester (2), mp 94°–95° C.; IR: (KBr): 420 (NH), 1710 (C=O), 1632 (C=O), 1600 (C=C). NMR (CDCl₃)δ: 8.19 and 7.5 (d, J=12 Hz, 4H, ArH), 6.93 (br, s, 1H, NH), 6.20 (s, 1H, H—C=C), 5.75 (s, 1H, H—C=C), 5.30 (s, 2H, OCH₂).

Anal. Calcd. for C₁₅H₁₈N₂O₆ C: 55.0: H, 5.63: N: 8.69. Found: C: 55.85; H: 5.67; N: 8.65.

(b) Using DCC

To a suspension of Boc-Ser.OBzl(NO$_2$) (1) (6.0 g, 0.0176 mol) and CuCl (1.8 g, 0.018 mol) in CHCl$_3$ (180 ml) was added dicyclohexylcarbodiimide (DCC: 4.9 g, 0.0216 mol) with ice cooling and the mixture was stirred for 3 days at room temperature. Water (200 ml) was added to the reaction mixture and additional stirring was continued for 3 min when the CHCl$_3$ layer was separated and the aqueous layer was extracted with CHCl$_3$. The combined CHCl$_3$ layer was washed with water, dried over Na$_2$SO$_4$ and evaporated in vacuo. The resulting residue was chromatographed by elution with benzene (silica gel 60–200 mesh, 40 g, Baker Analyzed) to give 4.1 g, (72.3%) of Boc-dehydroalanine-p-nitrobenzyl ester (2), mp 94°–96° C.

EXAMPLE III p-Nitrobenzyl-3-t-butoxycarbonylaminopyrazoline-3-carboxylate (3)

To a solution of Boc-dehydroalanine-p-nitrobenzyl ester (2) (700 mg, 2.2 mmol) in CH$_2$Cl$_2$ (10 ml) was added dropwise ethereal CH$_2$N$_2$ solution (prepared from Diazald, 4.12 g, 19 mmol) in Et$_2$O (40 ml) over a period of 40 min with ice cooling. After stirring for 1 hr at 0 5° C., excess of CH$_2$N$_2$ was decomposed by addition of CaCl$_2$ at room temperature and the mixture was filtered. The filtrate was evaporated in vacuo to give a white solid and the solid was triturated with n-hexane and then filtered by suction to give 3 (710 mg: 88.5%), mp 79°–80° C. Recrystallization from AcOEt-n-hexane gave pure p-Nitrobenzyl-3-t-butoxycarbonylaminopyrazoline-3-carboxylate (3) as colorless prisms, mp 84° C. (dec.); IR: (KBr) 3270 (NH), 1700–1740 (C=O), 1600 (N=N). NMR(CDCl$_3$)δ: 8.2 and 7.45 (dd, 4H, ArH H), 6.38 (s, 1H, NH), 5.29 (s, 2H, OCH$_2$), 4.4–52 (m, 2H, NCH$_2$), 1.95–2.25 (m, 2H, CH$_2$), 1.40 (s, 9H, Boc).

Anal Calcd. for C$_{16}$H$_{20}$N$_4$O$_6$: C: 52.74; H: 5.53; N: 15.38. Found: C: 52.62; H: 5.59; N: 15.34.

EXAMPLE IV

Boc-Cyclopropylalanine p-nitrobenzyl Ester (4)

A mixture of the pyrazoline, p-nitrobenzyl-3-t-butoxycarbonylaminopyrazoline-3-carboxylate (3) (550 mg), and benzene (10 ml) was refluxed for 1.5 hr (bath temp., ca 90° C.) and the benzene was removed in vacuo to give a solid, which was recrystallized from AcOEt-n-hexane to afford 508 mg of Boc-cyclopropylalanine p-nitrobenzyl ester (4) (100%); mp 117°–118° C.; IR (KBr) 3350 (NH), 1730 (C=O), 1680 (C=O). NMR (CDCl$_3$)δ: 8.2 and 7.48 (AB d, 4H, ArH), 5.2 (s, 2H, OCH$_2$), 5.15 (br, s, 1H, NH), 1.00–1.75 (m, 4H, CH$_2$x2), 1.44 (s, 9H, Boc).

Anal. Calcd. for C$_{16}$H$_{20}$N$_2$O$_6$: C: 57.14; H: 5.99; N: 8.33. Found: C: 57.05; H: 5.99; N: 8.31.

EXAMPLE V

Boc-Cyclopropyl Alanine (5)

To a solution of Boc-cyclopropylalanine p-nitrobenzyl Ester (4) (450 mg, 1.34 mmol) in MeOH (20 ml) was added 1N NaOH (2.6 ml, 2.6 mmol) at room temperature. After the mixture was stirred for 3 hr, water (10 ml) was added and the MeOH was removed in vacuo. The aqueous residue was washed with Et$_2$O to remove p-nitrobenzyl alcohol and the aqueous layer was separated, cooled in an ice bath and 10% citric acid solution was added to pH 3. The mixture was saturated with NaCl and extracted with AcOEt and the extracts were washed with sat. NaCl solution, dried over Na$_2$SO$_4$ and evaporated in vacuo to give a white solid which was recrystallized from AcOEt-n-hexane to afford 260 mg of Boc-cyclopropyl Alanine (5) (96.3%) as colorless needles, mp 176°–177° C. (dec.); IR (KBr): 3230(NH), 1630-1680 (C=O). NMR (CDCl$_3$+DMSO)δ: 9.45 (br, s, 1H, COOH), 5.88 (br, s, 1H, NH) 1.3–1.7 (m, 2H, CH$_2$), 1.0–1.2 (m, 2H, CH$_2$), 1.50 (s, 9H, Boc).

Anal. Calcd. for C$_9$H$_{15}$NO$_4$ C: 53.72; H: 7.51; N: 6.96. Found: C: 53.59; H: 7.58; N: 6.88.

EXAMPLE VI

Diazoisobutane (6)

To a solution of isobutylurea (2.0 g, 0.017 mol) in HOAc/H$_2$O (6:1) (6 ml) was added dropwise 4.8 M NaNO$_2$ solution (6 ml) with ice cooling over 1 hr. After stirring was continued for an additional 1 hr, water (20 ml) was added to the reaction mixture and the yellow crystals were extracted into CHCl$_3$. The extract was washed with water and evaporated at 25° C. to dryness giving a yellow solid. The resulting crude nitroso compound was dissolved in Et$_2$O (20 ml) and the solution was added dropwise to the mixture of 40% KOH solution (5.4 ml) and Et$_2$O (20 ml) at −15° C. to −20° C. over a 1 hr period. The reaction mixture was stirred for 1 hr at the same temperature and the Et$_2$O layer containing diazoisobutane (6) was separated and used in the next reaction immediately.

EXAMPLE VII p-Nitrobenzyl 3-t-Butoxycarbonylamino-5-isopropylpyrazoline-3-carboxylate (7)

The ethereal diazoisobutane (6) was gradually added to a solution of Boc-dehydroalanine-p-nitrobenzyl ester (2) (967 mg, 3 mmol) in CH$_2$Cl$_2$ (15 ml) at −10° C. to −15° C. with stirring. After stirring for 1 hr at the same temperature, the solvent was evaporated in vacuo and the resulting residue was triturated with hexane and filtered by suction to give 1.2 g of p-nitrobenzyl p-nitrobenzyl 3-t-butoxycarbonylamino-5-isopropylpyrazoline-3-carboxylate (7) (98.4%) mp 78°–79° C. (dec.). Recrystallization from AcOEt-n hexane gave colorless prisms having mp 87°–89° C. (dec.); IR (KBr) 3390(NH), 1745(C=O), 1690(C=O), 1605 (N=N).NMR (CDCl$_3$)δ: 8.2 and 7.5 (d, d, 4H, ArH), 6.2 (br s, 1H, NH); 5.30 (s, 2H, OCH$_2$), 4.8–5.2 (m, 1H, CH—N=N), 1.5–2.3 (m, 3H, (CH$_3$)$_2$CH and CH$_2$), 1.35 (s, 9H, Boc), 1.00–1.30 (m, 3H, CH$_3$), 0.8–1.10 (m, 3H, CH$_3$).

Anal. Calcd. for C$_{19}$H$_{26}$N$_4$O$_6$: C: 56.15; H: 6.45; N: 13.79. Found: C: 55.93; H: 6.53; N: 13.75.

EXAMPLE VIII

Boc-Cyclopropyl Leucine p-Nitrobenzyl Ester (8)

The pyrazoline, p-nitrobenzyl 3-t-butoxycarbonylamino-5-isopropylpyrazoline-3-carboxylate (7) (1.1 g, 2.7 mmol), was dissolved in benzene (20 ml), the solution was refulxed for 2 hr and evaporated in vacuo to give a white solid which was recrystallized from AcOEt-n-hexane giving colorless prisms of Boc-cyclopropyl leucine p-nitrobenzyl ester (8), 950 mg (95%), mp 139°–143° C., IR (KBr) 3360(NH), 1725(C=O), 1680 (C═O). NMR (CDCl$_3$)δ: 8.20 and 7.52 (d,d, 4H, ArH), 5.25 (s,2H,OCH$_2$), 5.22 (br,s,1H,NH), 1.2–1.8 (m,4H,CH$_2$,CHx2), 1.4 (s,9H,Boc), 0.8–1.15 (m,6H,(CH$_3$)$_2$CH).

Anal. Calcd. for C$_{19}$H$_{26}$N$_2$O$_6$: C: 60.30; H: 6.93; N: 7.40. Found: C: 59:73; H, 7.05;, N, 8.27.

EXAMPLE IX

Boc-Cyclopropyl-Leucine (9)

To a suspension of Boc-cyclopropyl leucine p-nitrobenzyl ester (8) (300 mg, 7.9 mmol) in MeOH (20 ml) was added 2N NaOH soln. (7 ml) under ice cooling and the mixture was stirred for 3 hr at room temperature, the starting material gradually dissolved and the mixture turned yellow. Water (10 ml) was added and the MeOH was evaporated in vacuo. The aqueous residue was washed with AcOEt, cooled in an ice bath and acidified by the addition of 10% citric acid to pH 3. The resulting white precipitate was extracted with AcOEt (3×20 ml) and the extract was washed with sat. NaCl soln, dried over Na$_2$SO$_4$, and evaporated in vacuo. The resulting of Boc-cyclopropyl-leucine (9) was recrystallized from AcOEt-n-hexane to give 140 mg, (72.5%) as colorless prisms; mp 196°–197° C. (dec.); IR: (KBr) 3230(NH), 1690(C═O), 1645(C═O). NMR (CDCl$_3$+DMSOd$_6$) δ:5.78 (s, 1H, NH), 1.2–1.8 (m,4H,CH$_2$, CHx2),1.4 (s,9H,Boc), 0.9–1.1 (m,6H,(CH$_3$)$_2$CH).

Anal. Calcd. for C$_{12}$H$_{21}$NO$_4$: C: 59.24; H: 8.70; N: 5.76. Found: C: 59.28; H: 8.74; N: 5.72.

EXAMPLE X

Benzaldehyde p-Toluenesulfonyl Hydrazone (10)

A mixture of benzaldehyde (5.25 g, 0.05 mol), p-toluenesulfonyl hydrazide (9.3 g, 0.05 mol) and AcOH (20 ml) was stirred for 15 min at 70° C., and allowed to stand overnight at room temperature. Et$_2$O (20 ml) was added to the mixture, the precipitated solid was triturated with ether and the crystals were filtered by suction and washed with Et$_2$O to give Benzaldehyde p-Toluenesulfonyl Hydrazone (10), 9.7 g (70.7%), mp 126°–128° C. (dec.).

EXAMPLE XI

Boc E-Cyclopropyl Phenylalanine p-Nitrobenzyl Ester (11)

Sodium (138 mg, 6 mmol) was dissolved in ethylene glycol (10 ml) and the tosylhydrazone, benzaldehyde p-toluenesulfonyl hydrazone (10), 823 mg, (3 mmol) was added to the solution. When dissolution was completed, hexane (20 ml) was added and the mixture was refluxed for 20 min (bath temp. 85°–90° C.) with vigorous stirring. Then the mixture was cooled in an ice bath and the resulting red colored product was extracted with cold n-hexane (20 ml×3). The combined extracts were washed with 1N NaOH soln. (20 ml), sat. NaCl soln. (20 ml) and then dried over Na$_2$SO$_4$. After filtering, the pink filtrate was added to a mixture of Boc-dehydroalanine-p-nitrobenzyl ester (2) (322 mg, 1 mmol) in CH$_2$Cl$_2$ (10 ml) over a period of 15 min at 0° C. The mixture was stirred overnight at room temperature and the red color disappeared. The solvent was evaporated in vacuo and the residue was triturated with n-hexane-ether. The resulting solid was filtered by suction to give Boc E-cyclopropyl Phenylalanine p-nitrobenzyl ester (11) (380 mg, 92.2%); mp 115°–116° C.; IR: (KBr) 3390(NH), 1715(C═O). NMR (CDCl$_3$)δ: 8.1 and 7.1 (dd,4H,ArH), 7.1–7.50 (m,5H,ArH), 5.45 (br.s,1H,NH),4.9 (s, 2H,CH$_2$O), 2.8–3.1 (m,1H,CH), 2.0–2.4, 1.2–1.8 (m,2H,CH$_2$), 1.45 (s, 9H, Boc).

EXAMPLE XII

Boc E-Cyclopropyl Phenylalanine (12)

A mixture of Boc E-cyclopropyl phenylalanine p-nitrobenzyl Ester (11) (200 mg, 0.485 mmol), MeOH (10 ml) and 2N NaOH soln. (3 ml) was stirred overnight at room temperature. Water (10 ml) was added and the MeOH was evaporated in vacuo. The residue was washed with AcOEt and the aqueous layer was cooled in an ice bath and acidified with 10% citric acid to pH 3. The mixture was saturated with NaCl and extracted with AcOEt. The extract was washed with sat. NaCl soln, dried over Na$_2$SO$_4$ and evaporated in vacuo. The resulting solid was recrystallized from AcOEt-n-hexane to give Boc E-cyclopropyl phenylalanine (12) (90 mg, 67.2%) as colorless prisms, mp 158°–160° C. (dec.); NMR (CDCl$_3$)δ: 7.2–7.4 (m, 5H, ArH), 2.7–2.9 (m, 1H, CH), 2.0–2.3 and 1.5–1.7 (m, 2H, CH$_2$), 1.5 (s, 9H, BOC). NMR identical with that of earlier sample.

EXAMPLE XIII p-Nitrobenzyl 3-t-Butoxycarbonylamino-5-(N-tosylindol-3-yl)-pyrazoline-3-carboxylate (13)

A solution of N-tosylindol-3-yl diazomethane (3 mml) in CH$_2$Cl$_2$ (20 ml) is added to a solution of Boc-dehydroalanine-p-nitrobenzyl ester (2) in 20 ml CH$_2$Cl$_2$ at −15° C. After stirring 1 hr at −15° C. and 4 hr at 25° C., the solution is evaporated to dryness and the residue is triturated with hexane. The solid product, p-nitrobenzyl 3-t-butoxycarbonylamino-5-(N-tosylindol-3-yl)pyrazoline-3-carboxylate (13), is recrystallized from ethyl acetate-hexane to constant melting point. NMR (DCDl$_3$)δ: 4.8–5.4 (m, 1H, CH—N═N).

EXAMPLE XIV

Boc Cyclopropyl Tryptophan p-Nitrobenzyl Ester (14)

The pyrazoline, p-nitrobenzyl 3-t-butoxycarbonylamino-5-(N-tosylindol-3-yl)-pyrazoline-3-carboxylate (13), (1 mmole) is suspended in toluene (50 ml) and the mixture is refluxed until its NMR spectrum shows the presence of cyclopropane protons (δ3.0–3.5 and 0.8–1.2 ppm) and the loss of the pyrazoline peak at δ5.0. (2 hr). The solution is evaporated and the residue of Boc cyclopropyl tryptophan p-nitrobenzyl ester (14) is crystallized from ethylacetate-hexane. NMR (DCDl$_3$)δ: 2.7–3.0 (m, 1H, CH), 2.0–2.3 and 1.5–1.7 (m, 2H, CH$_2$).

EXAMPLE XV p-Nitrobenzyl 3-t-Butoxycarbonyl-5-(3-chloropropyl)-pyrazoline-3-carboxylate (15)

4-Chlorobutyraldehyde tosylhydrazone (3 mmole) is added to a solution of sodium (6 mmole) in ethylene glycol (15 ml). Hexane (25 ml) is added and the mixture is stirred 30 min at 90° C. After cooling, the diazo-compound is extracted into cold hexane (3×20 ml). The combined extracts are washed with 1N NaOH (20 ml) and saturated NaCl solution (25 ml) and dried over anhyd. Na$_2$SO$_4$. After filtration, the filtrate is added to a mixture of Boc-dehydroalanine-p-nitrobenzyl ester (2) (1 mmole) in CH$_2$Cl$_2$ (10 ml) at 0° C. over a 15-minute period. After stirring at 25° C. for 16 hr, the solution is evaporated and the residue is triturated with $Et_2O$-hexane. The solid pyrazoline, p-nitrobenzyl 3-t-butoxycarbonyl-5-(3-chloropropyl)-pyrazoline-3-carboxylate (15), is crystallized from ethyl acetate-hexane. NMR ($CDCl_3$)δ: 4.5–5.4 (m, 1H, CH—N=N).

EXAMPLE XVI

Boc 3-(3-Chloropropyl) Cyclopropyl Alanine p-Nitrobenzyl Ester (16)

The pyrazoline, p-nitrobenzyl 3-t-butoxycarbonyl-5-(3-chloropropyl)pyrazoline-3-carboxylate (15), (1 mmole) is suspended in toluene (50 ml) and the mixture is refluxed until its NMR spectrum shows the presence of cyclopropane protons (δ30.0–3.5 and 0.8–1.2 pmm) and the loss of the pyrazoline peak at δ5.0 (2 hr). The solution is evaporated and the residue of Boc 3-(3-Chloropropyl) cyclopropyl alanine p-nitrobenzyl ester (16) is crystallized from ethyl acetate-hexane. NMR ($CDCl_3$) δ:2.7–3.0 (m, 1H, CH), 2.0–2.3 and 1.5–1.7 (m, 2H, $CH_2$).

EXAMPLE XVII

Boc Cyclopropyl Lysine p-Nitrobenzyl Ester (17)

The cyclopropyl alanine derivative Boc 3-(3-Chloropropyl) cyclopropyl alanine p-nitrobenzyl Ester (16) is treated with a 1M solution of ammonia in isopropanol at 50° C. in a sealed pressure bottle for 48 hrs. Evaporation of the solution gives a solid residue which is dissolved in warm ethyl acetate (5 ml) and the solution is washed with saturated NaCl solution (3×25 ml) and dried over anhyd. $Na_2SO_4$. Evaporation of the solution gives Boc cyclopropyl lysine p-nitrobenzyl ester (17) which recrystallized from ethyl acetate-hexane. NMR ($CDCl_3$) δ: 1.2–1.8 (m, 5H, $CH_2CH_2CH$), 0.8–1.1 (m, 2H, $CH_2$), 2.5 (m, 2H, $CH_2NH_2$).

EXAMPLE XVIII p-Nitrobenzyl 3-t-Butoxycarbonylamino-5-(4-[2,4-dinitrophenoxyl]-phenyl)pyrazoline-3-carboxylate (18)

A solution of 4-(2,4-dinitrophenoxy)-phenyldiazomethane in $CH_2Cl_2$ (20 ml) is added to a solution of Boc-dehydroalanine-p-nitrobenzyl ester (2) in 20 ml $CH_2Cl_2$ at −15° C. After stirring 1 hr at −15° C. and 4 hr at 25°, the solution is evaporated to dryness and the residue is triturated with hexane. The solid product, p-nitrobenzyl 3-t-butoxycarbonylamino-5-(4-[2,4-dinitrophenoxyl]-phenyl)-pyrazoline-3-carboxylate (18), is recrystallized from ethyl acetate-hexane to constant melting point. NMR ($CDCl_3$)δ: 4.8–5.4 (m, 1H, CH—N=N).

EXAMPLE XIX

Boc-O-2,4-dinitrophenyl Cyclopropyl Tyrosine p-Nitrobenzyl Ester (19)

The pyrazoline, p-nitrobenzyl 3-t-butoxycarbonylamino-5-(4-[2,4-dinitrophenoxyl]-phenyl)-pyrazoline-3-carboxylate (18), is suspended in toluene (50 ml) and the mixture is refluxed until its NMR spectrum shows the presence of cyclopropane protons (δ3.0–3.5 and 0.8–1.2 ppm) and the loss of the pyrazoline peak at δ5.0 (2 hr). The solution is evaporated and the residue of Boc-0-2,4-dinitrophenyl cyclopropyl tyrosine p-nitrobenzyl ester (19) is crystallized from ethylacetate-hexane. NMR ($CDCl_3$δ: 2.7–3.0 (m, 1H, CH), 2.0–2.3 and 1.5–1.7 (m; 2H, $CH_2$).

EXAMPLE XX

Boc Cyclopropyl Tyrosine p-Nitrobenzyl Ester (20)

A solution of Boc O-2,4-dinitrophenyl cyclopropyl tyrosine p-nitrobenzyl ester (19) (1 mmole) in DMF (2 ml) is treated with 2-mercaptoethanol (20 mmole). After 1 hr at 25° C. the DMF was evaporated and the residue of Boc cyclopropyl tyrosine p-nitrobenzyl ester (20) is crystallized from ethyl acetate-hexane. NMR ($CDCl_3$)δ: 2.7–2.9 (m, 1H, CH), 2.0–2.3, 1.5–1.7 (m, 2H, $CH_2$).

EXAMPLE XXI

Z-(2RS)-$\nabla^E$Phe-Leu.OMe, (21)

A solution of isobutyl chloroformate (546 mg, 4 mmol) in chloroform (10 ml) was added dropwise to a solution of Boc-Ser.OBzl($NO_2$) (1) (1.24 g, 4 mmol) and N-methylmorpholine (404 mg, 4 mmol) in chloroform (30 ml) at 0.5° C. After stirring for 20 min, a solution of Leu.OMe.HCl (1.45 g, 8 mmol) and N-methylmorpholine (0.81 g, 8 mmol) in chloroform (20 ml) was added at 10° C. After stirring for 2 hr at 0.5° C. and then overnight at room temperature, the reaction mixture was washed with $H_2O$, 5% citric acid and 5% $NaHCO_3$ successively, and dried over $Na_2SO_4$. The solvent was evaporated in vacuo and the residue was recrystallized from ethylacetate-hexane to give Z-(2RS)-$\nabla^E$Phe-Leu.OMe, (21) (1.13 g, 64.4%) as colorless needles, mp 94°–97° C. $R_f(I)=0.85$, $R_f(III)=0.12$.

Anal. Calcd. for $C_{25}H_{30}N_2O_5$: C, 68.47; H, 6.90; N, 6.39. Found: C, 68.50; H, 6.99; N, 6.38.

Separation of Z-(2RS)-$\nabla^E$Phe-Leu.OMe, (21) into Diastereomers by HPLC

Z-(2RS)-$\nabla^E$Phe-Leu.OMe, (21) was separated into its diastereoisomers using HPLC ($C_{18}$ Lichrosorb, 20 cm×0.46 cm, $CH_3CN$-$H_2O$ (55:45), 2 ml/min). The (2S)$\nabla^E$Phe isomer showed $t_R=6.2$ min and the (2R)$\nabla^E$Phe isomer showed $t_R=8.1$ min.

EXAMPLE XXII (2S)-$\nabla^E$Phe-Leu.OMe.TFA (22)

A solution of Z-(2S)-$\nabla^E$Phe-Leu.OMe (1.31 g, 3 mmol) and thioanisole (2 ml) in trifluoroacetic acid (TFA) (20 ml) was stirred at 0° for 3 hr, and then room temperature overnight. The TFA was removed under reduced pressure, and the residue was triturated with ether (30 ml) and the precipitated crystals were collected by suction and washed with ether to give (2S)-$\nabla^E$Phe-Leu.OMe.TFA (22) (1.14 g, 91.2%), mp 251°–2° (dec.); $[\alpha]^D-89.6°$ (C=0.5 $H_2O$). NMR ($CF_3CO_2$-H—$CDCl_3$(1:1)δ: 0.67 (6H, br s ($CH_3$)), 0.78–1.40 (3H, m, $CH_2CH$), 2.28 (2H, d, J = 10 Hz, 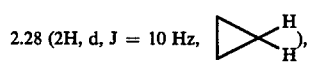), 3.50 (1H, t, J=Hz, $H\nabla$), 3.85 (3H, s, $CH_3O$), 4.20–4.50 (1H, m, $CHCO_2Me$), 5.66–5.88 (1H, m, NH), 7.53 (5H, s, ArH), 7.70–8.20 (2H, br, $NH_3$). $R_f(IV)=0.74$.

Anal. Calcd. for $C_{19}H_{25}F_3N_2O_5$: C, 54.54; H, 6.02; N, 6.70. Found: C, 54.61; H, 6.05; N, 6.66.

EXAMPLE XXIII

Z-(2S)-∇$^E$Phe-Leu.OMe (23)

A solution of Z(2S)∇$^E$Phe (1.24 g, 4 mmol) and Leu.OMe.HCl (1.09 g, 6 mmol) in THF (50 ml) was chilled to 0° C. and triethylamine (0.61 g, 6 mmol), HOBt (0.54 g, 4 mmol) and DCC (0.83 g, 4 mmol) were added successively at )° with stirring. After stirring for 4 hr at 0° C. and room temperature overnight, the precipitated crystals were filtered and the filtrate was evaporated in vacuo. The residue was extracted with ethyl acetate and the extract was washed with 5% citric acid, 5% NaHCO$_3$ and water successively, and then dried over Na$_2$SO$_4$. The solvent was removed under reduced pressure and the resulting solid was recrystallized from ethyl acetate-hexane to give Z-(2S)-∇$^E$Phe-Leu.OMe (23) (1.48 g, 84.5%) as a colorless needles, mp 114°–115° C.; [α]$^{25}$ –132.1° (c=1.0, MeOH). NMR (CDCl$_3$) δ: 0.78 6H, d, J=6 Hz, (CH$_3$)$_2$CH), 1.10–1.70 (4H, m, CH—CH$_2$ and H), 2.18 (1H, d of d, J=9 Hz, and 6 Hz, ∇ H), 2.80 (1H, t, J=9 Hz, Ph $^H$ ∇), 3.56 (3H, s, CH$_3$O), 4.17–4.45 (1H, m, CHCO$_2$Me), 5.25 (2H, s, PhCH$_2$O), 5.56–5.80 (1H, br, NH), 6.60–6.95 (1H, br, NH), 7.33 (5H, br s, Ph ∇), 7.47 (5H, s, PhCH$_2$). R$_f$(I)=0.85, R$_f$(IV)=0.12.

Anal. Calcd. for C$_{25}$H$_{30}$N$_2$O$_5$: C, 68.47; H, 6.90; N, 6.39. Found: C, 68.53; H, 6.93; N, 6.35.

EXAMPLE XXIV

Z-(2S)-∇$^E$Phe-Leu.OMe (24)

Following the same procedure as above for Z-(2S)-∇$^E$Phe-Leu.OMe (23), Z-(2R)-∇$^E$Phe (1.24 g, 4 mmol) and Leu.OMe.HCl (1.09 g, 6 mmol) was treated with Et$_3$N (0.61 g, 6 mmol), HOBt (0.54 g, 4 mmol) and DCC (0.83 g, 4 mmol) in THF (50 ml) to give Z-(2S)-∇$^E$Phe-Leu.OMe (24) (1.41 g, 80.5%) as prisms (ethyl acetate-hexane); [α]$_D^{25}$ 87.6° (C=1.0, MeOH); NMR (CDCl$_3$) : 0.57 (3H, d, J=6 Hz, CH$_3$), 0.68 (3H, d, J=6 Hz, CH$_3$), 0.70–1.45 (4H, m, CH$_2$CH, ∇ H), 2.25 (1H, d of d, J=9 Hz and 6 Hz, ∇∖H), 2.77 (1H, t, J = 9 Hz 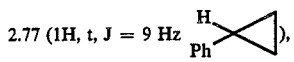), 3.65 (3H, s, CH$_3$O), 4.15–4.50 (1H, m, CHCO$_2$Me), 5.27 (2H, s, PhCH$_2$O), 5.73 (1H, s, NH), 6.83–7.15 (1H, br, NH), 7.32 (5H, br s Ph—CH—), 7.55 (5H, s, PhCH$_2$). P$_f$(I)=0.85, R$_f$(III)=0.12.

Anal. Calcd. for C$_{25}$H$_{30}$N$_2$O$_5$: C, 68.47; H, 6.90; N, 6.39. Found: C, 68.30; H, 6.96; N, 6.32.

EXAMPLE XXV

(2R)-∇$^E$Phe-Leu.OMe.TFA (25)

Following a procedure similar to that above for (2S)-∇$^E$Phe-Leu.OMe.TFA (22), Z(2R)∇$^E$Phe (1.31 g, 4 mmol) was treated with thioanisole (2 ml) and TFA (20 ml) to give (2R)-∇$^E$Phe-Leu.OMe.TFA (25) (1.09 g, 87%), mp 256°–257° C. (dec.); [α]$_D^{22}$ 24,2.°, NMR (CDCl$_3$—CF$_3$CO$_2$H (1:1)) δ: 0.83 (6H, d, J =4 Hz, CH$_3$), 1.05–1.53 (3H, m, CH$_2$CH),

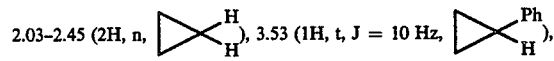

3.75 (3H, s, CH$_3$O), 4.23–4.52 (1H, m, CHCO$_2$Me), 5.80 (1H, d, J=8 Hz, NH), 7.52 (5H, s, ArH), 7.80–8.20 (2H, br NH). R$_f$(IV)=0.77, R$_f$(V)=0.80.

Anal. Calcd. for C$_{19}$H$_{25}$F$_3$N$_2$O$_5$: C, 54.54; H, 6.02; N, 6.70. Found: C, 54.56; H, 6.06; N, 6.66.

EXAMPLE XXVI

Z-D-Ala-Gly-OMe (26)

A solution of Z-D-Ala (2.23 g, 10 mmol) and Gly.O-Me.HCl (1.26 g, 10 mmol) in THF (50 ml) was chilled to 0° C. and triethylamine (1.01 g, 10 mmol), HOBt (1.35 g, 10 mmol) and DCC (2.06 f, 10 mmol) was added successively at 0° C. with stirring. After stirring for 4 hrs at 0° C., the reaction mixture was stirred at room temperature overnight and the precipitated crystals were filtered and the filtrate was evaporated in vacuo. The residue was extracted with ethyl acetate and the extract was washed with 5% citric acid, 5% NaHCO$_3$ and water successively, and dried over anhyd. Na$_2$SO$_4$. The solvent was removed in vacuo and the resulting solid was recrystallized from ethyl acetate-hexane to give Z-D-Ala-Gly-OMe (26) (2.48 g, 84.4%) as colorless needles, mp 96°–97° C.; [α]$_D^{22}$23.3° (c=1.0, MeOH): NMR (CDCl$_3$)δ:1.39 (3H, d, J=8 Hz, CH$_3$), 3.76 (3H, s CH$_3$O), 4.03 (2H, d, J=6 Hz, CH$_2$NH), 4.15–4.50 (1H, m, —CH—NH), 5.15, (2H, s, CH$_2$O), 5.58 (1H, d, J=7 Hz, NH), 6.70–6.95 (1H, br, NH), 7.42 (5H, s, Ar—H). R$_f$(I)=0.62, R$_f$(VI)=0.38.

Anal. Calcd. for C$_{14}$H$_{18}$N$_2$O$_5$: C, 57.14; H, 6.16; N, 9.52. Found: C, 57.19; H, 6.20; N, 9.50.

EXAMPLE XXVII

Z-Tyr-D-Ala-Gly-OMe (27)

A suspension of Z-D-Ala-Gly-OMe (26) (5.88 g, 0.02 mmol) and 10% Pd-C (0.4 g) in methanol (300 ml) was stirred under a hydrogen atmosphere at room temperature for 1.5 hr. The catalyst was filtered and the filtrate was evaporated in vacuo. The residue and Z-Tyr (6.30 g, 0.02 mol) was dissolved in dry THF (300 ml), cooled to 0° C. and HOBt (2.70 g, 0.02 mol) and DCC (4.12 g. 0.02 mol) were added successively at 0° C. The solution was stirred for 3 hr at 0° C. and overnight at room temperature. The precipitated crystals were filtered. The filtrate was evaporated under reduced pressure, the residual crystals were dissolved in EtOAc and the solution was washed with 5% NaHCO$_3$, 0.2 N Hcl and water, and dried over anhyd. Na$_2$SO$_4$. The solvent was removed in vacuo and the resulting solid was purified by silica gel column chromatography using CHCl$_3$—CH$_3$OH (98:2) as eluant to give Z-Tyr-D-Ala-Gly-OMe (27) (8.62 g, 94.3%), mp 154°–155° C. (AcO-Et-hexane); [α]$_D^{22}$ 33.4° (C=1.0, MeOH); NMR (CDCl$_3$-DMSO-d$_6$ (4:1) δ: 1.25 (3H, d, J=7 Hz, CH$_3$), 2.82–3.03 (2H, m, CH$_2$,), 3.70 (3H, s, CH$_3$O), 3.80–3.95 (2H, m, CH$_2$PhOH), 4.15–4.60 (2H, m, 2 CH), 5.05 (2H, s, CH$_2$O), 6.70–7.25 (4H, m, ArH), 6.70–6.90 (1H, br, NH), 7.36 (5H, s, ArH), 7.70–8.10 (2H, br, NH). R$_f$(I)=0.48; R$_f$(VI)=0.08.

Anal. Calcd, for C$_{23}$H$_{27}$N$_3$O$_7$: C, 60.39; H, 5.95; N, 9.18. Found: C, 60.23; H, 6.00; N, 9.08.

EXAMPLE XXVIII

Z-Tyr-D-Ala-Gly.OH (28)

To a solution of Z-Tyr-D-Ala-Gly-OMe (27) (4.57 g, 0.01 mol) in MeOH (10 ml) was added 1 N NaOH (20 ml, 0.02 mol) at 0° with stirring. The suspension was stirred for 2 hr at 0° C., diluted with water (80 ml), and neutralized with 1 N HCl (20 ml). The precipitated crystals were collected by suction, washed with water and dried under reduced pressure to give Z-Tyr-D-Ala-Gly.OH (28) (3.59 g, 81.0%), mp 102°–104° C. (AcOEt) (lit.* mp 124° C.); $[\alpha]_D^{22}$ 18.0° (C=1.0, DMF), (lit.* $[\alpha]_D^{22}$ 16.7° (c=0.54, DMF)); NMR (DMSO-d$_6$)δ: 1.16 (3H, d, J=7 Hz, CH$_3$), 2.60–2.90 (2H, m, CH$_2$), 3.80 (2H, d, J=6 Hx, CH$_2$PhOH), 4.10–4.45 (2H, m, 2CH), 5.02 (2H, s, CH$_2$O), 6.63–7.20 (4H, m, HOPh-), 7.40 (5H, s, ArH), 8.10–8.30 (2H, br, 2 NH), 9.10–9.40 (1H, br, OH). R$_f$(IV)=0.20.

*S. Shinagawa, M. Fujino, H. Ishii and K. Kawai, Chem. Pharm. Bull., 29, 3630 (1981).

Anal Calcd. for C$_{22}$H$_{25}$N$_3$O$_7$: C, 59.59; H, 5.68; N, 9.48. Found: C, 59.32; H, 5.79; N, 9.39.

EXAMPLE XXIX

Z-Tyr-D-Ala-Gly(2S)-∇$^E$Phe-Leu.OMe(29)

To a solution of Z-Tyr-D-Ala-Gly.OH (887 mg, 2 mmol) and (2S)-∇$^E$Phe-Leu.TFA (836 mg, 2 mmol) in THF (80 ml) was added N-methylmorpholine (202 mg, 2 mmol) HOBt (270 mg, 2 mmol) and EDC (1-ethyl-3(3-dimethylaminopropyl)-carbodiimide.HCl) (384 mg, 2 mmol) succesively at 0° C. After stirring for 3 hr at 0° C. and overnight at room temperature, the solvent was removed under reduced pressure, and the residue was extracted three times with 100 ml of AcOEt. The combined AcOEt extracts were washed with 5% NaHCO$_3$, 0.2 N HCl, water, and dried over anhyd. Na$_2$SO$_4$. The solvent was removed under reduced pressure, and the solid was recrystallized from ethylacetate-hexane to give 1.212 g (83%) of Z-Tyr-D-Ala-Gly(2S)-∇$^E$Phe-Leu.OMe(29) as a colorless powder, mp 162°–163° C.; $[\alpha]_D$ −56.8° (c=0.5, DMF). NMR (DMSO-d$_6$) δ: 0.78 (6H, t, J=5 Hz, CH$_3$×2), 1.00–1.67 (4H, m, CH$_2$CH and cyclopropyl-H), 1.18 (3H, d, J=7 Hz, CH$_3$), 1.90–2.15 (1H, m, cyclopropyl-H), 2.46–3.00 (3H, m, CH$_2$ and cyclopropyl-H), 3.48 (3H, s, CH$_3$O), 3.70–3.80 (2H, br, CH$_2$) 3.95–4.43 (3H, m, 3 CH), 5.01 (2H, s, CH$_2$), 6.67–7.18 (4H, m, HOPh-), 7.32 (5H, s, ArH), 7.40 (5H, s, Ar-H), 7.30–7.60 (1H, m, NH), 7.72 (1H, d, J=8 Hz, NH), 8.10–8.40 (2H, m, 2 NH), 8.68 (1H, s, NH), 9.28 (1H, s, OH). R$_f$(II)=0.79; R$_f$(IV)=0.63.

Anal. Calcd. for C$_{39}$H$_{47}$N$_5$O$_9$: C, 64.18; H, 6.49; N, 9.60. Found: C, 64.04; H, 6.54; N, 9.56.

EXAMPLE XXX

Z-Tyr-D-Ala-Gly-(2R)-∇$^E$Phe-Leu.OMe (30)

Following a procedure similar to that described for Z-Tyr-D-Ala-Gly (2S)-∇$^E$Phe-Leu.OMe(29), Z-Tyr-D-Ala-Gly.OH (887 mg, 2 mmol), (R)-∇$^E$Phe-Leu.OMe.TFA (836 mg, 2 mmol), N-methylmorpholine (202 mg, 2 mmol), HOBt (270 mg, 2 mmol), EDC (384 mg, 2 mmol), and THF (80 ml) gave 1.287 g (88.2%) of Z-Tyr-D-Ala-Gly-(2R)-∇$^E$Phe-Leu.OMe (30) as a colorless powder, mp 168°–170° C. (AcEOt-hexane). NMR (DMSO-d$_6$) δ: 0.53 (3H, d, J=5 Hz, CH$_3$), 0.73 (3H, d, J=5 Hz, CH$_3$), 1.20 (3H, d, J=6 Hz, CH$_3$), 1.05–1.45 (4H, m, CH$_2$CH and ∇H), 1.87–2.13 (1H, m, ∇H), 2.43–2.60 (1H, m, ∇H), 2.60–2.90 (3H, m, CH$_3$), 3H, s, CH$_3$O), 3.70–3.85 (2H, br, CH$_2$), 3.90–4.45 (3H, m, CHx3), 5.03 (2H, s, CH$_2$), 6.66–7.23 (4H, m, HOPh)7.31 (5H, s, ArH), 7.40 (5H, s, ArH), 7.40–7.85 (2H, m, NHx2), 8.15–8.40 (2H, br, NHx2), 8.70 (1H, s, NH), 9.25 (1H, s, OH). R$_f$(II)=0.81, R$_f$(IV) 0.63.

Anal, Calcd, for C$_{39}$H$_{47}$N$_5$O$_9$: C, 64.18; H, 6.49; N, 9.60. Found: C, 63.99; H, 6.51; N, 9.56.

EXAMPLE XXXI

Z-Tyr-D-Ala-Gly-(2S)∇$^E$Phe-Leu.OH (31)

Z-Tyr-D-Ala-Gly-(2S)-∇$^E$Phe-Leu.OMe (29) (365 mg, 0.5 mmol) was dissolved in methanol (1 ml), the solution was cooled in an ice-water bath and 1 N NaOH (1 ml, 1 mmol) at 0° C. was added. After stirring for 2 hr at 0° C., the solution was neutralized with 1N HCl and diluted with water. The precipitated solid was collected by suction and dried under reduced pressure. The solid was purified by silica gel column chromatography using chloroform-methanol (19:1) and chloroform-methanol-acetic acid (95:5:1) as eluants. After starting material was removed using CHCl$_3$/MeOH (19:1), Z-Tyr-D-Ala-Gly-(2S)∇$^E$Phe-Leu.OH (31) 230 mg (64%), mp 153°–155° C. (AcOEt). R$_f$(IV)=0.48; Rf(V)−=0.88; $[\alpha]_D^{22}$ −98.2° (c 0.5, DMF), was eluded with CHCl$_3$:MeOH:HOAc (95:5:1).

Anal. Calcd. for C$_{38}$H$_{45}$N$_5$O$_9$.H$_2$O: C, 62.20; H, 6.46; N, 9.54. Found: C, 62.39; H, 6.50, N, 9.30.

EXAMPLE XXXII

Z-Tyr-D-Ala-Gly-(2R)∇$^E$Phe-Leu.OH (32)

According to a procedure similar to that described above, Z-Try-D-Ala-Gly-(2R)∇$^E$Phe-Leu.OMe (30) (365 mg, 0.5 mmol) gave 270 mg (75%) of Z-Tyr-D-Ala-Gly-(2R)∇$^E$Phe-Leu.OH (32), mp 204°–205° C. (AcOEt); Rf(IV)=0.40; Rf (V)=0.80; $[\alpha]_D^{22}$ −41.2° (c 0.5, DMF).

Anal. Calcd. for C$_{38}$H$_{45}$N$_5$.H$_2$O: C, 62.20; H, 6.46, N, 9.54. Found: C, 62.28; H, 6.46; N, 9.38.

EXAMPLE XXXIII

Tyr-D-Ala-Gly-(2S)∇$^E$Phe-Leu (33)

A solution of Z-Tyr-D-Ala-Gly-(2S)∇$^E$Phe-Leu.OH (31) (143 mg, 0.2 mmol) and thioanisole (0.3 ml) in trifluoroacetic acid (TFA) (3 ml) was stirred 1 hr at 0° C., and 4 hr at room temperature. The solvent was removed under reduced pressure and the residue was triturated with ether to give a TFA salt. This salt was dissolved in 5% AcOH and passed through a column containing a large excess of Amberlite CG400 (acetate form), followed by a column of BioGel P-2 (1.9×8.9 cm, 200 400 mesh) (4 ml/20 min). The fractions containing Tyr-D-Ala-Gly-(2S)∇$^E$Phe-Leu (33) were pooled and lyophilized to give 70 mg (60.1%) of (S)-10, mp 197° C. (dec.); ret. time=4.4 min (HPLC, C$_{18}$-Lichrosorb (20 cm×0.46 cm), CH$_3$CN: H$_2$O:TFA (30:70:1), 1 ml/min); R$_f$(IV)=0.05; R$_f$(V)0.38 $[\alpha]_D^{22}$ −7.12° (c, 0.25 AcOH). Amino acid ratios in acid hydrolyzate: Tyr 0.94; Ala 0.92; Gly 1.0; Leu 1.01; [(2S)∇$^E$Phe was not detected].

Anal. Calcd. for C$_{36}$H$_{39}$N$_5$O$_7$.0.8 H$_2$O: C, 60.45; H, 6.86; N, 11.74. Found: C, 60.62; H, 6.89; N, 11.42.

EXAMPLE XXXIV

Try-D-Ala-Gly-(2R)∇$^E$Phe-Leu(34)

Following a procedure similar to that described above, Z-Tyr-D-Ala-Gly-(2R)∇$^E$Phe-Leu.OH (32) (0.43 mg, 0.2 mmol) gave 82 mg (70.4%) of (2R)-10, mp 185° C. (dec.); ret. time 8.1 min [HPLC, C$_{18}$-Lichrosorb (20 cm×0.46 cm), CH$_3$CN:H$_2$O:TFA (30:70:1), 1 ml/min]; Rf(IV)=0.03; Rf(V)=0.35; $[\alpha]_D^{22}$ 89.6 (c 0.25, AcOH). Amino acid ratios in acid hydrolazate: Tyr 0.91, Ala 0.98, Gly 1.0, Leu 0.95. [(2SR)∇$^E$Phe was not detected].

Anal. Calcd. for $C_{30}H_{39}N_5O_7 \cdot CH_3CO_2H$: 1.5 $H_2O$; C, 57.47; H, 6.93; N, 10.47. Found: C, 57.56; H, 6.67; N, 10.08.

The foregoing illustrates specific embodiments within the scope of this invention and is not to be construed as limiting said scope. While the invention has been described herein with regard to a certain specific embodiment, it is not so limited. It is to be understood that variations and modifications thereof may be made by those skilled in the art without departing from the scope of the invention.

What is claimed is:

1. A peptide resistant to enzymatic cleavage selected from the group consisting of:
   ∇Met-Leu-Phe,
   Met-∇Leu-Phe,
   pGln-His-∇Pro-NH$_2$,
   pGln-∇His-Pro-NH$_2$,
   ∇pGln-His-Pro-NH$_2$,
   ∇Tyr-Gly-Phe-Leu,
   ∇Tyr-D-Ala-Gly-Phe-Leu,
   ∇Tyr-D-Ala-Gly-Phe-Met,
   Tyr-Gly-Gly-Phe-∇Leu,
   Tyr-D-Ala-Gly-Phe-∇Leu,
   ∇Tyr-D-Ala-Gly-Phe-∇Leu,
   Tyr-Gly-Gly-Phe-∇Met,
   Tyr-D-Ala-Gly-Phe-∇Met,
   ∇Tyr-D-Ala-Gly-Phe-∇Met,
   ∇Tyr-Gly-Gly-Phe-∇Met,
   ∇Tyr-Gly-Gly-Phe-∇Leu,
   Ile-His-Pro-Phe-∇His-Leu,
   Pro-Phe-His-∇Leu-Leu-Val-Tyr,
   Pro-Phe-His-Leu-∇Leu-Val-Tyr,
   Asp-Arg-Val-Tyr-Ile-∇His-Pro-Phe,
   Asp-Arg-Val-∇Tyr-Ile-His-Pro-Phe,
   Asp-Arg-∇Val-Tyr-Ile-His-Pro-Phe,
   Asp-∇Arg-Val-Tyr-Ile-His-Pro-Phe,
   ∇Asp-Arg-Val-Tyr-Ile-His-Pro-Phe,
   Asp-Arg-Val-∇Tyr-Ile-∇His-Pro-Phe,
   Sar-Arg-Val-∇Tyr-Ile-His-Pro-Phe,
   Sar-Arg-Val-Tyr-Ile-∇His-Pro-Phe, and
   Sar-Arg-Val-∇Tyr-Ile-∇His-Pro-Phe.

2. A peptide according to claim 1, wherein said peptide is ∇Met-Leu-Phe.
3. A peptide according to claim 1, wherein said peptide is Met-∇Leu-Phe.
4. A peptide according to claim 1, wherein said peptide is pGln-His-∇Pro-NH$_2$.
5. A peptide according to claim 1, wherein said peptide is pGln-∇His-Pro-NH$_2$.
6. A peptide according to claim 1, wherein said peptide is ∇pGln-His-Pro-NH$_2$.
7. A peptide according to claim 1, wherein said peptide is ∇Tyr-Gly-Gly-Phe-Leu.
8. A peptide according to claim 1, wherein said peptide is ∇Tyr-D-Ala-Gly-Phe-Leu.
9. A peptide according to claim 1, wherein said peptide is ∇Tyr-D-Ala-Gly-Phe-Met.
10. A peptide according to claim 1, wherein said peptide is Tyr-Gly-Gly-Phe-∇Leu.
11. A peptide according to claim 1, wherein said peptide is Tyr-D-Ala-Gly-Phe-∇Leu.
12. A peptide according to claim 1, wherein said peptide is ∇Tyr-D-Ala-Gly-Phe-∇Leu.
13. A peptide according to claim 1, wherein said peptide is Tyr-Gly-Gly-Phe-∇Met.
14. A peptide according to claim 1, wherein said peptide is Tyr-D-Ala-Gly-Phe-∇met.
15. A peptide according to claim 1, wherein said peptide is ∇Tyr-D-Ala-Gly-Phe-∇Met.
16. A peptide according to claim 1, wherein said peptide is ∇Tyr-Gly-Gly-Phe-∇Met.
17. A peptide according to claim 1, wherein said peptide is ∇Tyr-Gly-Gly-Phe-∇Leu.
18. A peptide according to claim 1, wherein said peptide is Ile-His-Pro-Phe-∇His-Leu.
19. A peptide according to claim 1, wherein said peptide is Pro-Phe-His-∇Leu-Leu-Val-Tyr.
20. A peptide according to claim 1, wherein said peptide is Pro-Phe-His-Leu-∇Leu-Val-Tyr.
21. A peptide according to claim 1, wherein said peptide is Asp-Arg-Val-Tyr-Ile-∇His-Pro-Phe.
22. A peptide according to claim 1, wherein said peptide is Asp-Arg-Val-∇Tyr-Ile-His-Pro-Phe.
23. A peptide according to claim 1, wherein said peptide is Asp-Arg-∇Val-Tyr-Ile-His-Pro-Phe.
24. A peptide according to claim 1, wherein said peptide is Asp-∇Arg-Val-Tyr-Ile-His-Pro-Phe.
25. A peptide according to claim 1, wherein said peptide is ∇Asp-Arg-Val-Tyr-Ile-His-Pro-Phe.
26. A peptide according to claim 1, wherein said peptide is Asp-Arg-Val-∇Tyr-Ile-∇His-Pro-Phe.
27. A peptide according to claim 1, wherein said peptide is Sar-Arg-Val-∇Tyr-Ile-His-Pro-Phe.
28. A peptide according to claim 1, wherein said peptide is Sar-Arg-Val-Tyr-Ile-∇His-Pro-Phe.
29. A peptide according to claim 1, wherein said peptide is Sar-Arg-Val-∇Tyr-Ile-∇His-Pro-Phe.

* * * * *

UNITED STATES PATENT AND TRADEMARK OFFICE
CERTIFICATE OF CORRECTION

PATENT NO. : 4,629,784
DATED : December 16, 1986
INVENTOR(S) : Charles H. Stammer It is certified that error appears in the above-identified patent and that said Letters Patent are hereby corrected as shown below:

Claim 1, column 23, line 22, change "∇Tyr-Gly-Phe-Leu" to

--∇Tyr-Gly-Gly-Phe-Leu--.

Claim 14, column 24, line 20, change "Tyr-D-Ala-Gly-Phe-∇met" to --Tyr-D-Ala-Gly-Phe-∇Met--.

Signed and Sealed this

Twenty-eighth Day of April, 1987

Attest:

DONALD J. QUIGG

Attesting Officer — Commissioner of Patents and Trademarks